(12) United States Patent
    Pridgen

(10) Patent No.: US 12,280,162 B2
(45) Date of Patent: Apr. 22, 2025

(54) VEHICLE SANITATION SYSTEM

(71) Applicant: James Pridgen, Whiteville, NC (US)

(72) Inventor: James Pridgen, Whiteville, NC (US)

(*) Notice: Subject to any disclaimer, the term of this patent is extended or adjusted under 35 U.S.C. 154(b) by 861 days.

(21) Appl. No.: 17/345,841

(22) Filed: Jun. 11, 2021

(65) Prior Publication Data

US 2022/0008580 A1    Jan. 13, 2022

Related U.S. Application Data

(60) Provisional application No. 63/048,859, filed on Jul. 7, 2020.

(51) Int. Cl.
| *A61L 2/10* | (2006.01) |
| *A61L 2/24* | (2006.01) |
| *A61L 2/26* | (2006.01) |

(52) U.S. Cl.
CPC ............. *A61L 2/10* (2013.01); *A61L 2/24* (2013.01); *A61L 2/26* (2013.01); *A61L 2202/14* (2013.01); *A61L 2202/16* (2013.01)

(58) Field of Classification Search
CPC .......... A61L 2/10; A61L 9/20; A61L 2202/25; A61L 2202/16; A61L 2202/11
See application file for complete search history.

(56) References Cited

U.S. PATENT DOCUMENTS

| 6,787,782 | B1 | 9/2004 | Krosney et al. |
| 9,144,618 | B2 | 9/2015 | Kreitenberg |
| 9,662,410 | B2 | 5/2017 | MacKin |
| 10,376,605 | B1 | 8/2019 | Majdali et al. |
| 2015/0090903 | A1* | 4/2015 | Cole .................... A61L 2/24 250/492.1 |
| 2017/0100989 | A1 | 4/2017 | Chapaton et al. |
| 2020/0061223 | A1* | 2/2020 | Hallack ................ B60N 2/002 |
| 2021/0393818 | A1* | 12/2021 | Kanigowski .......... A61L 2/10 |

* cited by examiner

*Primary Examiner* — Regina M Yoo
(74) *Attorney, Agent, or Firm* — Boudwin Intellectual Property Law, LLC; Daniel Boudwin

(57) ABSTRACT

A vehicle sanitation system is provided. The vehicle sanitation system has a housing that can be removably secured to a back of a vehicle seat via a fastener, such as a strap. An ultraviolet emitting light is disposed in the housing and is positioned to emit ultraviolet light in order to encompass a passenger area of a vehicle when illuminated. The ultraviolet emitting light is in communication with a controller which can keep track of the amount of time that has elapsed since the ultraviolet emitting light last illuminated. A display on a from side of the housing is in communication with the controller, and the display can indicate the amount of time that has elapsed since the ultraviolet emitting light last illuminated. In this manner, a potential passenger can determine how much time has elapsed since the system last sanitized the passenger area of the vehicle through ultraviolet radiation.

7 Claims, 2 Drawing Sheets

VEHICLE SANITATION SYSTEM

CROSS REFERENCE TO RELATED APPLICATIONS

This application claims the benefit of U.S. Provisional Application No. 63/048,859 filed on Jul. 7, 2020. The above identified patent application is herein incorporated by reference in its entirety to provide continuity of disclosure.

BACKGROUND OF THE INVENTION

The present invention relates to sanitation devices used for a vehicle. More particularly, the present invention pertains to a sanitation system that utilizes ultraviolet radiation, such as UV-3 or UVC light, to eliminate harmful pathogens and sanitize a rear passenger compartment of an automobile. Such contagions can linger for long periods of time and can be the source of illness spreading from an infected person to an uninfected person (especially from passenger to driver).

Many people utilize ride-sharing services when running errands, traveling to and from an airport, or getting around in a new city. These ride sharing services consist of individuals with their own means of transportation, or businesses with fleets of automobiles. Once contacted, the ride-sharing service sends out a driver to pick-up a passenger-client and transport them to a desired location. Once the passenger-client reaches their destination, the driver proceeds to the next passenger-client. The passenger-client typically sits in a rear passenger compartment of the automobile being utilized. Thus, the rear passenger compartment becomes a type of shared space in that multiple people from all walks of life may utilize it over the span of a day, week, or so on. Such people may be suffering from various illnesses, whether symptomatic or not. If the person is suffering from such an illness, contagions can be spread on surfaces that the person comes into contact with. Such contagions can linger for long periods of time and can be the source of illness spreading from an infected person to an uninfected person.

Devices have been disclosed in the known art that relate to sanitation systems. These include devices that have been patented and disclosed in patent application publications. However, the devices in the known art have several drawbacks. Various devices and safeguards can be used to attempt to stem the tide of contagions flowing from one person to the next. Some people utilize facemasks and gloves when traveling in public spaces, but a large population does not. Some people utilize cleaning wipes prior to entering an automobile, but it can be very difficult to thoroughly clean and sanitize a large area such as a passenger compartment. Some drivers of ride-sharing services attempt to clean out their automobiles between passenger-clients, but such a process can be exhausting and take a long time to thoroughly clean and sanitize the passenger compartment. Additionally, even where the driver cleans the passenger compartment, the passenger-client may be unaware that such a cleaning has been done or may be unaware of how long it has been since the last cleaning. Where a passenger is unsure about their safety and well-being, such as whether they may be exposed to contagions, they are more likely to seek alternate means of transportation and forego the ride-sharing service.

The present invention substantially diverges in design elements from the known art and consequently it is clear that there is a need in the art for an improvement to existing sanitation system devices. In this regard the present invention substantially fulfills these needs.

SUMMARY OF THE INVENTION

In view of the foregoing disadvantages inherent in the known types of sanitation system devices now present in the art, the present invention provides a vehicle sanitation system. The present invention provides a sanitation system that utilizes ultraviolet radiation, such as UVC or UV-3 light to eliminate harmful pathogens and sanitize a rear passenger compartment of an automobile. A display indicates the last time the passenger compartment has been sanitized to alert and inform the passenger-client. The system includes a housing configured to be secured to a back of a vehicle seat via one or more straps. The housing includes an electronic display that indicates the last time the system was activated. In one embodiment, the housing includes UV-3 lights that are positioned to face the passenger compartment and when activated sanitize the area. The lights can be powered via a battery and can be charged via a connection to the vehicle power supply or a different connection. The device can be remotely operated and activated to sanitize the area after a passenger leaves and before accepting new passengers. In some embodiments, a ventilation system is disposed in the housing such that the UV-3 light can be shown on air entering into and exiting out of the housing as well as the passenger compartment.

Other objects, features, and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
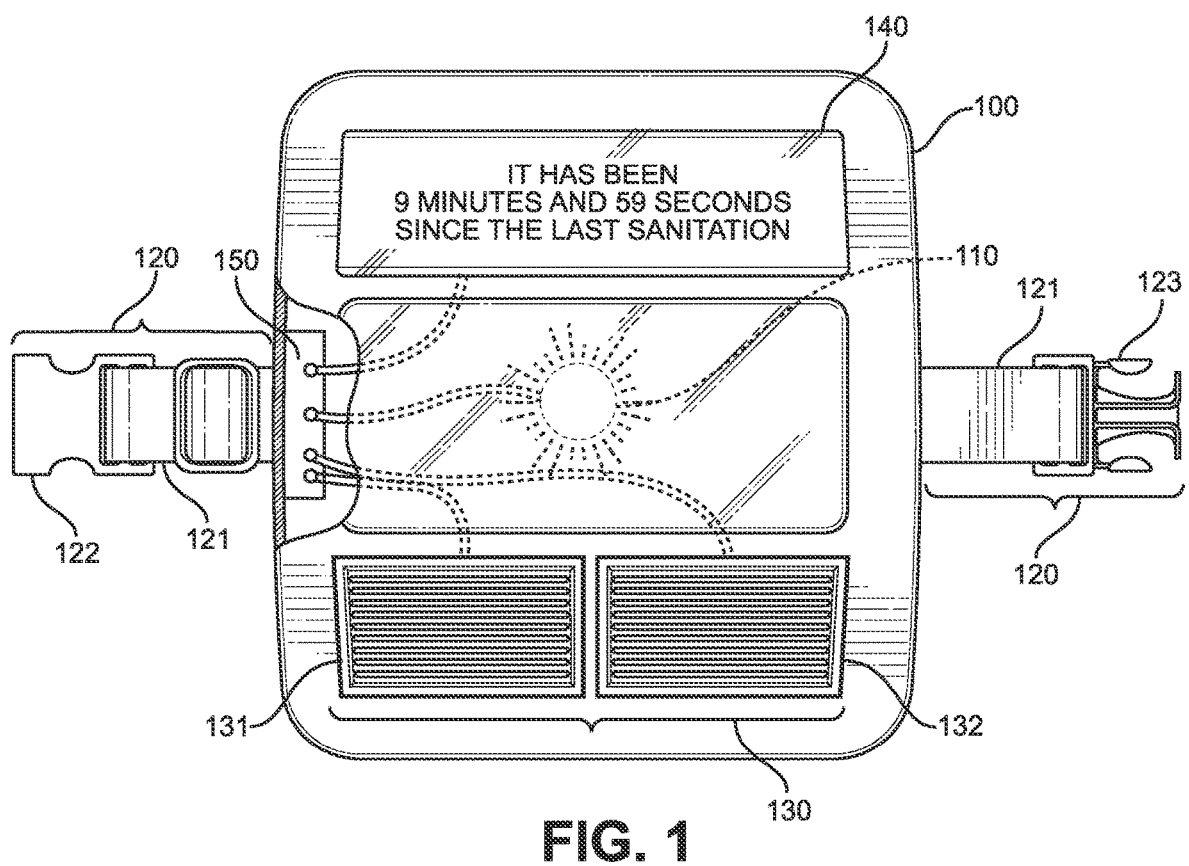
FIG. 1 shows a front view of a housing in an embodiment of the vehicle sanitation system.

Reference is made herein to the attached drawings. Like reference numerals are used throughout the drawings to depict like or similar elements of the vehicle sanitation system. For the purposes of presenting a brief and clear description of the present invention, a preferred embodiment will be discussed as used for the vehicle sanitation system. The figures are intended for representative purposes only and should not be considered to be limiting in any respect.

Figure 2:
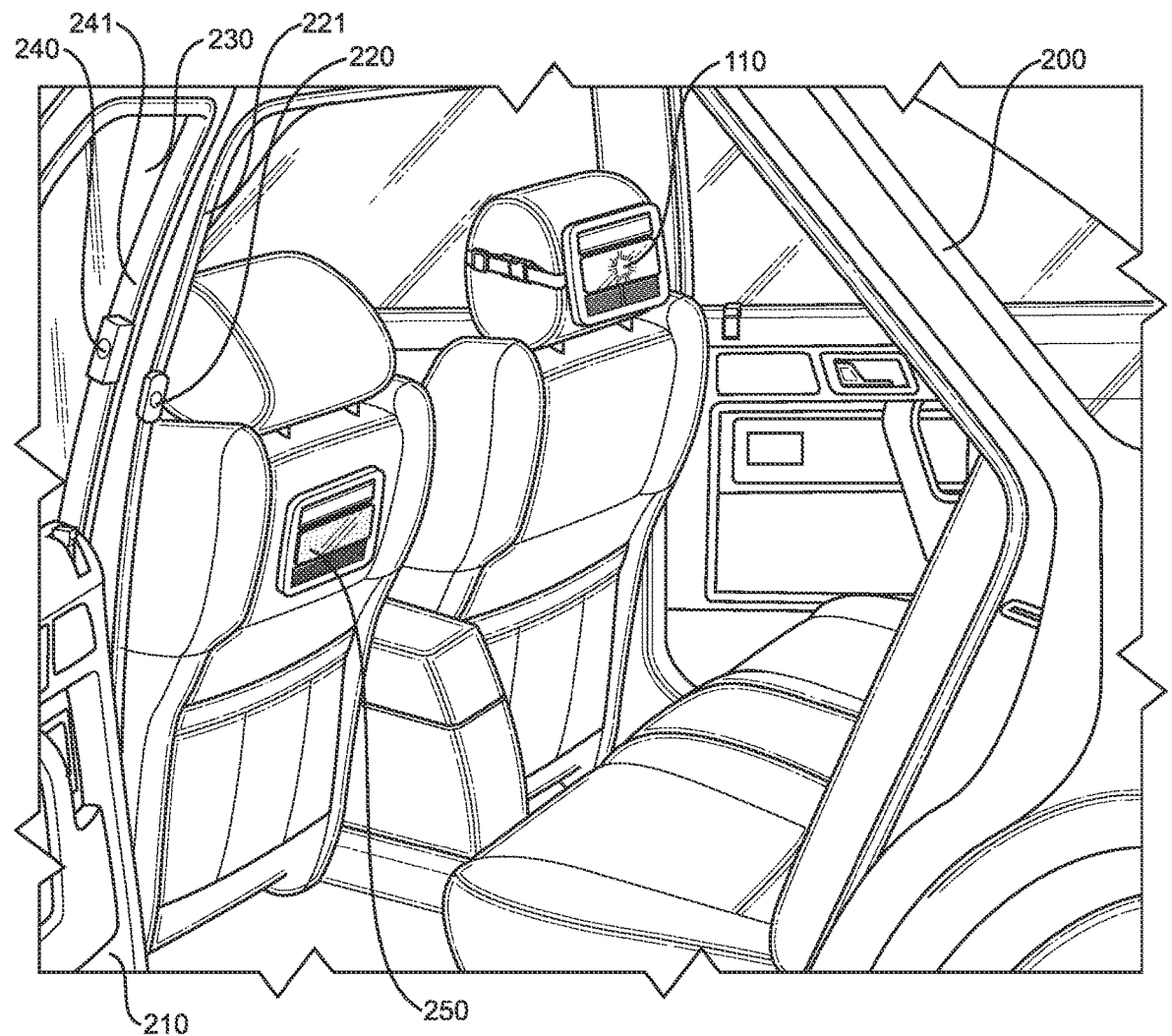
FIG. 2 shows a perspective view of an embodiment of the vehicle sanitation system in use.

Referring now to FIG. 1, there is shown a front view of a housing in an embodiment of the vehicle sanitation system. The vehicle sanitation system comprises a housing 100 with at least one ultraviolet emitting light 110 disposed therein. In some embodiments, the housing 100 is sized and shaped to be integrated into a vehicle seat (as shown in FIG. 2) while in other embodiments, the housing 100 is configured to be removably secured to a back of a vehicle seat via at least one fastener 120. In various embodiments, the housing 100 can be attached anywhere in the vehicle, such as armrests and seatbacks associated with the vehicle seat. However, in the preferred embodiment, the housing 100 is configured to secure to a back of a front vehicle seat headrest (as shown in FIG. 2). Additionally, in various embodiments, the housing 100 is sized to accommodate the ultraviolet emitting light 110 as well as a ventilation system 130, a display 140, a controller 150, and a wireless transceiver. In one embodiment, the system is powered by a battery. The ultraviolet emitting light 110, the ventilation system 130, the display 140, the controller 150, and the wireless transceiver are in communication with each other, and in the shown embodiment, are in electrical communication with each other. In other embodiments, the ultraviolet emitting light 110 can be charged and/or powered via a connection to the vehicle's pre-existing power supply or similar type of connection.

In the shown embodiment, the fastener 120 includes a pair of straps 121 with a female buckle member 122 and a complementary male buckle member 123 disposed on opposing sides of the housing 100 to form a snap-fit buckle. In the shown embodiment, a user is able to selectively adjust the length of the fastener 120 and ensure that the housing 100 is secured against a desired surface, such as a vehicle seat or a vehicle seat headrest (as shown in FIG. 2) by wrapping the straps 121 around the desired surface and adjusting the length of the straps 121. In this manner, the housing 100 can be secured such that the ultraviolet emitting light 110 is facing in a desired orientation. The present disclosure is not limited to such a fastener 120, and various types of fasteners including but not limited to snaps, buttons, adhesive peel and stick pads, and hook and loop fasteners are contemplated by the present disclosure. One of ordinary skill in the art will understand how the housing 100 can be removably secured to a desired surface through such a variety of fasteners 120.

The housing 100 includes at least one ultraviolet emitting light 110 disposed therein. In various embodiments, the ultraviolet emitting light 110 is configured to emit illumination categorized as UVC, UV3, or similar spectrums of light. Such spectrums of light have been shown to be effective at sanitizing surfaces, and therefore it is an object of the present invention to provide at least one ultraviolet emitting light 110 that is capable of sanitizing a surface by killing or eliminating undesired elements such as viruses, bacteria, or other germs, through such illumination. The ultraviolet emitting light 110 can be positioned, via securement of the housing 100 to the vehicle seat, such that the ultraviolet emitting light 110 faces a passenger compartment of the vehicle (as shown in FIG. 2). Thus, the ultraviolet emitting light 110 is positioned to emit ultraviolet light encompassing a passenger area of the vehicle when illuminated. In various embodiments, the ultraviolet emitting light 110 is adjustably positionable within the housing 100 such that an angle that the ultraviolet emitting light 110 is facing can be selectively adjustable to best suit the needs of the user. In a further embodiment the ultraviolet emitting light 110 is pivotally secured within the housing 100.

In some embodiments, the passenger area of the vehicle is a rear seating area of the vehicle. In other embodiments, the passenger area of the vehicle is a single passenger seat, or a portion thereof. In some embodiments, the passenger area is a passenger compartment of the vehicle defined by an area in which a passenger can rest while a driver controls the vehicle. In the preferred embodiment, the passenger area is a rear seating area of the vehicle defined between a rear of the front seats of the vehicle and a front of the back-most seats of the vehicle. In one embodiment, the ultraviolet emitting light 110 can illuminate every surface of the passenger compartment, and thereby expose such surfaces to illumination and radiation from the ultraviolet emitting light 110. In some embodiments, multiple ultraviolet emitting lights 110 are utilized to ensure the entirety of the passenger compartment is thus illuminated and exposed to the ultraviolet light emissions.

In addition to the ultraviolet emitting light 110, in some embodiments, a ventilation system 130 is disposed in the housing 100. In further embodiments, the ventilation system 130 is disposed in the housing 100 such that an air flow can be accomplished by pulling surrounding air in through an inlet port 131 and out through an outlet port 132. Thus, in such embodiments, the ventilation system 130 further comprises at least one inlet port 131 and at least one outlet port 132. In the shown embodiment, the ventilation system 130 is disposed on a bottom portion of the housing 100 and is configured to pass the air in front of the ultraviolet emitting light 110. In some embodiments, the ultraviolet emitting light 110 illuminates a space external to the housing 100 and the air flows through the illumination as it enters the inlet port 131 and exits the outlet port 132, thereby ensuring that the air is exposed to the ultraviolet illumination twice. In other embodiments, at least one ultraviolet emitting light 110 is disposed in an interior volume of the housing 100 and the air passes in front of such an internal ultraviolet emitting light 110. In some embodiments, the ventilation system 130 is integrated into the headrest and/or armrests of the vehicle seat. In other embodiments, the ventilation system 130 is a pump or similar circulatory system, such as a pre-existing HVAC system in the vehicle. In further embodiments, HEPA filters can be incorporated to further clean the air as the air circulates through the system.

The ultraviolet emitting light 110 is in communication with the controller 150. In one embodiment, the controller 150 is a control circuit. The controller 150 is configured to keep track of a time that has elapsed since the ultraviolet emitting light 110 last illuminated. Thus, in some embodiments, the controller 150 further comprises a time tracking device such as a timer. The controller 150, in turn, is in communication with the display 140. In some embodiments, the display 140 comprises an electronic and/or digital readout. The display 140 is disposed on a front side of the housing 100 such that a user can observe the output on the display 140 easily. The display 140 is configured to indicate the amount of time that has elapsed since the ultraviolet emitting light 110 last illuminated. In one embodiment, the display 140 can indicate, in real-time, the amount of time that has elapsed since the system was last activated. In the shown embodiment, for example, the display 140 indicates that "it has been 9 minutes and 59 seconds since the last sanitation" and can accurately indicate the amount of time elapsing in real-time as the display 140 is in communication with the controller 150. In this manner, a potential or current passenger can be informed and reassured as to when the last sanitation cycle occurred.

Referring now to FIG. 2, there is shown a perspective view of an embodiment of the vehicle sanitation system in use. In some embodiments, the vehicle sanitation system further comprises at least one sensor disposed within an interior of the vehicle 200. In the preferred embodiment, the vehicle 200 is a car. However, other vehicles such as trucks, SUVs, and the like are also contemplated and are within the scope of the present disclosure. The sensor is in communication with the controller. In one embodiment, the sensor is configured to detect when a vehicle door 210 is open or partially open. In another embodiment, the sensor is configured to detect when a body part of an individual enters the vehicle 200 through the vehicle door 210. In a further embodiment, the sensor is a door sensor 220 and is disposed in a vehicle door frame 221. Similarly, in one embodiment, the sensor is configured to detect when a vehicle window 230 is opened or partially open. In another embodiment, the sensor is configured to detect when a body part of an individual enters the vehicle 200 through the vehicle window 230. In a further embodiment, the sensor is a window sensor 240 and is disposed in a vehicle window frame 241.

Ultraviolet lighting may be harmful to human skin, and therefore various embodiments of the system include safety features. In one embodiment, the ultraviolet emitting light 110 includes a protective cover 250 that blocks potential illumination and radiation when the system is not in use. In the shown embodiment, the protective cover 250 is an opaque cover that can be positioned to block any illumination from the ultraviolet emitting light 110. In some embodiments, the protective cover 250 can slide over an external surface of the ultraviolet emitting light 110. In other embodiments, the protective cover 250 can be removably secured over the ultraviolet emitting light 110. In some embodiments, the protective cover 250 can be operably connected to the sensor such that when the sensor is triggered, the protective cover 250 is automatically disposed over the ultraviolet emitting light 110, thereby protecting a potential passenger from being exposed to ultraviolet illumination and radiation.

In other embodiments, the ultraviolet emitting light 110 can flip up or slide out from a hidden position and slide back when the system is not in use. In some embodiments, sensors are disposed in the vehicle's doorways and windows, as detailed above, wherein the sensors are in communication with the controller. The sensor is configured to determine when the vehicle door 210 or vehicle window 230 is open or partially open, or when a body part of an individual is inserted therethrough. Upon such detection, the system can automatically shut off the ultraviolet emitting light no such that no illumination or radiation is projected from the ultraviolet emitting light 110. In another embodiment, the sensors are motion sensors, such that whereupon the sensor detecting movement, the controller is configured to turn off the ultraviolet illumination emitting light 110. In this manner, the system can be configured to automatically shut off, by utilizing signals from the sensor(s) which are in communication with the controller, in order to prevent exposure of ultraviolet illumination or radiation to an individual. In some embodiments, the system can be remotely activated and operated, via the wireless transceiver in communication with the controller, such that the vehicle can sanitize the area after a passenger leaves and before accepting new passengers, thereby providing a user with an additional level of control over the system. In such an embodiment, the user does not need to by physically present or inside the vehicle when the system is activated, thereby providing a safe operating distance for the user.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A vehicle sanitation system, comprising:
 a housing configured to be removably secured to a back of a vehicle seat via at least one fastener;
 at least one ultraviolet emitting light disposed in the housing;
 the at least one ultraviolet emitting light positioned to emit ultraviolet light encompassing a passenger area of a vehicle when illuminated;
 the at least one ultraviolet emitting light in communication with a controller;
 the controller configured to keep track of a time that has elapsed since the at least one ultraviolet emitting light last illuminated;
 a display disposed on a front side of the housing;
 the display in communication with the controller, wherein the display is configured to indicate the amount of time that has elapsed since the at least one ultraviolet emitting light last illuminated;
 a ventilation system disposed within the housing, wherein the ventilation system comprises at least one inlet port and at least one outlet port; and
 the ventilation system configured to pass an air in front of the at least one ultraviolet emitting light.

2. The vehicle sanitation system of claim 1, further comprising at least one sensor disposed within an interior of the vehicle, wherein the at least one sensor is in communication with the controller.

3. The vehicle sanitation system of claim 2, wherein the at least one sensor is disposed in a vehicle door frame.

4. The vehicle sanitation system of claim 2, wherein the at least one sensor is disposed in a vehicle window frame.

5. The vehicle sanitation system of claim 1, wherein the at least one ultraviolet emitting light can emit illumination in the group consisting of UVC light and UV light.

6. The vehicle sanitation system of claim 1, wherein the housing is integrated into the vehicle seat.

7. The vehicle sanitation system of claim 1, wherein the passenger area is a rear seating area of the vehicle.

* * * * *